United States Patent
Nakamura et al.

[11] Patent Number: 5,880,828
[45] Date of Patent: Mar. 9, 1999

[54] SURFACE DEFECT INSPECTION DEVICE AND SHADING CORRECTION METHOD THEREFOR

[75] Inventors: Hisato Nakamura, Sitama-ken; Yoshio Morishige; Tetsuya Watanabe, both of Honjo, all of Japan

[73] Assignee: Hitachi Electronics Engineering Co., Ltd., Tokyo, Japan

[21] Appl. No.: 898,598

[22] Filed: Jul. 22, 1997

[30] Foreign Application Priority Data

Jul. 26, 1996 [JP] Japan .................................. 8-214101

[51] Int. Cl.⁶ .................................................. G01N 21/00
[52] U.S. Cl. ............................. 356/237.3; 356/237.4; 356/237.5
[58] Field of Search ................................. 356/237, 426, 356/338, 446, 430–431, 237.3, 237.4, 237.5; 250/559.45, 559.46, 559.48, 559.47, 559.49, 548

[56] References Cited

U.S. PATENT DOCUMENTS

| | | | |
|---|---|---|---|
| 4,511,803 | 4/1985 | Ross et al. | 356/431 |
| 4,659,172 | 4/1987 | Cavan | 356/237 |
| 5,481,202 | 1/1996 | Frye, Jr. | 356/237 |

*Primary Examiner*—Robert Kim
*Assistant Examiner*—Amanda Merlino
*Attorney, Agent, or Firm*—Fay, Sharpe, Beall, Fagan, Minnich & McKee

[57] ABSTRACT

A surface defect inspection device according to the present invention is provided with an average value calculating means in which an article corresponding to an object to be inspected having a multiplicity of substantially uniformly distributed standard particles deposited thereon is scanned in a main scanning direction as a defect inspection object, detection values of the standard particles at every detecting pixel are obtained based on detection signals obtained from an optical sensor at respective scanning positions while assuming the standard particles as being defects and average values of every detecting pixel with regard to the detection values obtained at the respective scanning positions are calculated, and a shading correction means in which detection values of every detecting pixel obtained when the object to be inspected is inspected are subjected to shading correction for every detecting pixel based on the calculated average values of every detecting pixel.

10 Claims, 5 Drawing Sheets

FIG.4 (a)
| PIXEL No. | CORRECTION VALUE |
|---|---|
| 1 | 0.9123 |
| 2 | 0.9123 |
| 3 | 0.9123 |
| 4 | 0.9123 |
| 5 | 0.9123 |
| 6 | 0.9123 |
| ⋮ | ⋮ |
136
FIG.4 (b)
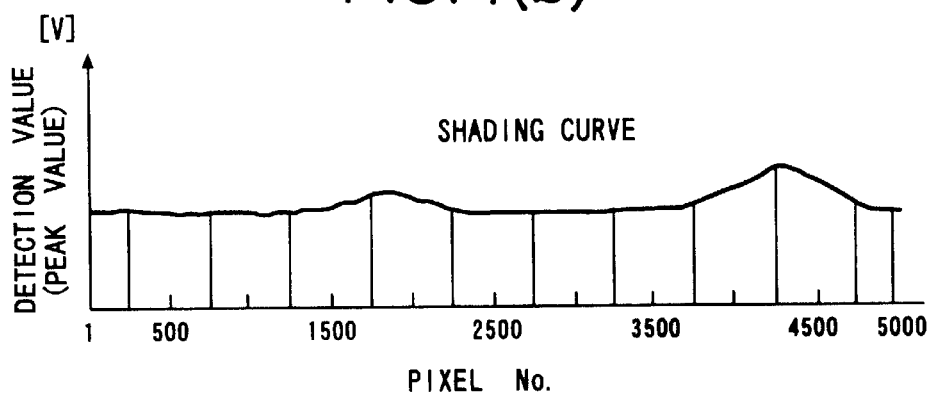
FIG.4 (c)
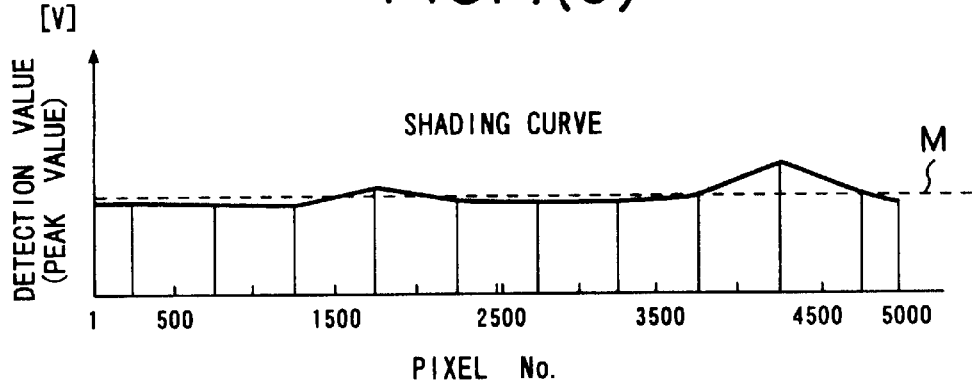

SURFACE DEFECT INSPECTION DEVICE AND SHADING CORRECTION METHOD THEREFOR

BACKGROUND OF THE INVENTION

1. Field of the Invention

The present invention relates to a surface defect inspection device and a shading correction method therefor, and, more specifically, relates to a method in which shading correction is performed for a line sensor in an extraneous substance detecting optical system in a semiconductor wafer extraneous substance inspection device, in which an extraneous substance is inspected by performing a main scanning on the wafer in the X axis (or Y axis) direction and a subscanning thereon in the Y axis (or X axis) direction, and an inspection device in which a surface defect is inspected after performing shading correction for the line sensor.

2. Background Art

The wafer extraneous substance inspection device, which is a surface defect inspection devices, includes two types: one is an XY scanning type in which a laser beam is irradiated over the surface of a wafer in the X and Y axis directions to scan the surface of the wafer, and the other is a rotary scanning type in which a wafer is rotated and a laser beam is irradiated over the surface of the rotating wafer to scan the surface of the wafer in a spiral or concentric circle shape.

In accordance with an improvement in integration degree for ICs, an improvement in inspection accuracy for a wafer recently has been demanded. Therefore, the wafer extraneous substance inspection device of the XY scanning type tends to be employed for the extraneous substance inspection. However, when the XY scanning type is employed as an in-line extraneous substance inspection device which is brought into a semiconductor manufacturing process to perform extraneous inspection, through-put for the inspection is reduced, and a problem arises that the device tends to be bulky.

As a countermeasure, which eliminates such drawbacks, improves the through-put of the inspection and reduces the size of the device, the present assignee has filed a U.S. patent application Ser. No. 08/678,069 in which long and narrow inspection regions are set in the subscanning direction, a main scanning for on-going is performed in a single axial direction with a large scanning width, and another main scanning for returning is performed after turning a wafer by 180°.

However, when setting the long and narrow regions in the subscanning direction as explained above in order to improve the through-put in the inspection, CCD sensors covering, for example, about 1,000~10,000 pixels are needed for a line sensor (unidimensional image sensor). Moreover, when such long and narrow light receiving elements are used, light receiving sensitivities for respective unit pixels are different and shading (difference in detection level due to difference of detection pixels) is generated in extraneous substance detection signals which prevents a further accurate extraneous substance detection. In particular, in a case that the size of extraneous substances is determined depending on the level of the detection signals, the shading of the optical sensor is a significant problem.

In a conventional shading correction method for light receiving signals from respective pixels in a wafer extraneous substance inspection device using CCD sensors, a wafer having a predetermined standard particle (such as a projection at a predetermined position on a wafer is used as a standard particle) is moved in a main scanning direction to thereby move the predetermined standard particle along the arrangement direction of the CCD sensors and to detect the standard particle therewith. Thereafter, the shading correction is performed so that the detection outputs for the respective pixels assume the same output value. However, in the CCD sensor setting a long and narrow inspection region in the subscanning direction as mentioned above, the main scanning direction does not correspond to the movement of the CCD sensors along the pixel arrangement direction. Moreover, since movement in the subscanning direction which runs along the pixel arrangement direction is effected with a predetermined width, it is impossible to obtain accurate detection values for the respective pixels from the predetermined standard particle over the long distance along the arrangement direction of the CCD sensors.

As a result, since it is impossible to obtain shading correction values for respective detected pixels based on the detection values for the corresponding pixels as in the conventional manner, it is difficult to perform shading correction for the CCD sensors arranged in the subscanning direction in the above mentioned type of devices.

SUMMARY OF THE INVENTION

An object of the present invention is to resolve the above coventional problems and to provide a surface defect inspection device in which shading correction can be effected for optical sensors even in the device including a scanning mechanism in which continuous movement of an object to be inspected in its movement direction is prevented with regard to the arrangement direction of detectable pixels of the optical sensors.

Another object of the present invention is to provide a shading correction method for a surface defect inspection device in which shading correction can be effected for optical sensors even in the device including a scanning mechanism in which continuous movement of an object to be inspected in its movement direction is prevented with regard to the arrangement direction of detectable pixels of the optical sensors.

A surface defect inspection device according to the present invention which achieves the above objects is characterized in that the surface defect inspection device comprises an average value calculating means in which an article corresponding to an object to be inspected having a multiplicity of substantially uniformly distributed standard particles deposited thereon is scanned in a main scanning direction as a defect inspection object, detection values of the standard particles by respective detecting portions in an optical sensor representing respective detecting pixels are obtained based on detection signals obtained from the optical sensor at respective scanning positions while assuming the standard particles as being defects, average values of the respective detecting portions in an optical sensor representing the respective detecting pixels with regard to the detection values obtained at the respective scanning positions are calculated, and a shading correction means in which detection values of the respective detecting portions representing the respective detecting pixels obtained when the object to be inspected is inspected are subjected to shading correction for the respective detecting portions representing the respective detecting pixels based on the calculated average values of the respective detecting portions representing the respective detecting pixels.

Further, a shading correction method according to the present invention is characterized in that the shading correction method comprises the steps of: obtaining detection values of the standard particles by respective detecting portions in an optical sensor representing respective detecting pixels based on detection signals obtained from the optical sensor at respective scanning positions while assuming the standard particles as being defects; calculating average values of the respective detecting portions representing the respective detecting pixels with regard to the detection values obtained at the respective scanning positions; and subjecting detection values of the respective detecting portions (representing the respective detecting pixels obtained when the object to be inspected is inspected) to shading correction for the respective detecting portions representing the respective detecting pixels based on the calculated average values of the respective detecting portions representing the respective detecting pixels.

Namely, at first the article having a multiplicity of substantially uniformly distributed standard particles deposited thereon is scanned and the detection values of the respective detecting portions at the respective scanning positions are obtained; then average values of the respective detection signal values of the respective detecting portions representing the respective detecting pixels are calculated and the respective average values are compared with a predetermined reference value; and then the comparison result can be treated as respective shading values for the respective detection signals of the detecting portions representing detecting pixels.

Thereafter, an average value calculated by averaging the respective average values obtained with the respective detecting portions representing the respective detecting pixels, or a maximum value or a minimum value among the respective averages, is determined as the above predetermined value to be used, and the respective detection signals are corrected by respective correction values through which the respective detection signal values assume the predetermined value so as to effect shading correction.

As a result, even with a surface defect inspection device having a scanning mechanism in which continuous movement of an object to be inspected is prevented with regard to the subscanning direction in which detecting pixels of an optical sensor are arranged, shading correction values for the respective detecting portions representing the respective detecting pixels are easily obtained and thereby the respective detection values are effected with shading correction. Accordingly, a detection without being affected by shading can be realized even if the width of inspection region in the subscanning direction is further enlarged, whereby inspection efficiency is improved. Further, a surface defect inspection device of the XY scanning type can be incorporated into a manufacturing process line.

BRIEF DESCRIPTION OF THE DRAWINGS

FIG. 4(a) is a view for explaining a shading correction value table;

FIG. 4(b) is a view for explaining a shading characteristic;

FIG. 4(c) is a view for explaining a shading characteristic when interpolation values are used.

DESCRIPTION OF THE PREFERRED EMBODIMENTS

Figure 1:
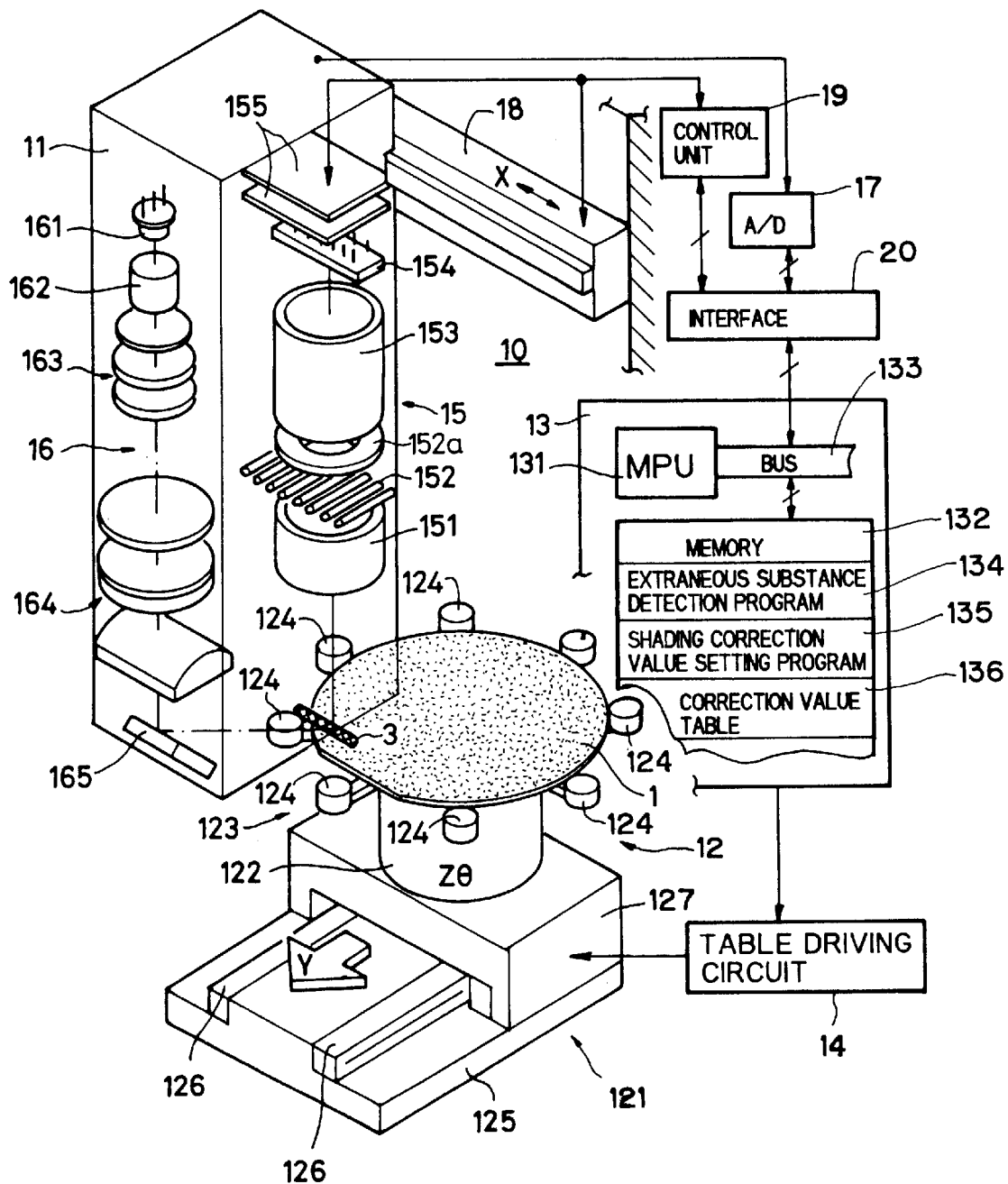
FIG. 1 is a construction diagram of one embodiment of a wafer extraneous substance inspection device including primarily a detection optical system to which a shading correction method according to the present invention is applied.

Numeral 10 in FIG. 1 is an extraneous substance inspection device which is constituted by an extraneous substance inspection optical system 11, an inspection table 12 disposed below the extraneous substance inspection optical system 11, a data processing and control unit 13, a table driving circuit 14, an A/D converter circuit (A/D) 17, an X direction moving mechanism 18, a control unit 19 and an interface 20. Numeral 1 is a wafer on which a multiplicity of substantially uniformly distributed standard particles are deposited and which is used for shading detection for respective detecting pixels in the form of the respective detecting portions in an optical sensor, and the wafer 1 is carried on the inspection table 12. The control unit 19 generates several control signals for driving the X direction moving mechanism 18 and a CCD control and signal reading circuit 155, for example, in response to signals from the data processing and control unit 13 via the interface 20. The shading detection use wafer (hereinbelow simply called a wafer) 1 is formed by depositing standard particles of about 3,000~10,000 pieces substantialy uniformly over the entire surface of a blank wafer.

The extraneous substance inspection optical system 11, as seen from the illustrated interior thereof, is constituted by a detection optical system 15 and a light projecting optical system 16, and the light projecting optical system 16 irradiates a laser beam at an inspection area 3 (extraneous substance detection area) on the wafer 1 having a predetermined width in the subscanning direction. The scattering light above the inspection area 3 is received and detected by the detection optical system 15 which is provided above the inspection table 12 in the vertical direction. The extraneous substance inspection optical system 11 is secured to the X direction moving mechanism 18 and is permitted to shift in the X direction (subscanning direction) by a predetermined pitch unit. The length of the inspection area 3 in the X direction corresponds to the width (scanning width in subscanning direction) of one line in the main scanning direction in the present embodiment. Therefore, the movement pitch in the subscanning direction (X direction) corresponds to the above indicated width.

The light projecting optical system 16 is constituted by a semiconductor laser source 161, condenser lens systems 162, 163 and 164 and a reflection mirror 165, and the laser beam is condensed in an elliptical form corresponding to the inspection area 3 and is irradiated onto the inspection area 3 on the wafer 1 with an elevation angle of about 30° as seen from the wafer 1.

The detection optical system 15 is constituted by an objective lens 151 facing the inspection area 3 on the wafer 1, a space filter 152 disposed behind the objective lens 151, a slit plate 152a with an aperture for eliminating stray light disposed behind the space filter 152, a condenser lens system 153 disposed behind the slit plate 152a, a CCD sensor 154 which is designed to receive an entire picture image of the inspection area 3 image-formed by the condenser lens system 153 and the CCD control, and signal reading circuit 155 which reads the detection signals from the CCD sensor 154. In the present embodiment the CCD sensor 154 is one line sensor having length corresponding to 5,000 pixels in subscanning direction.

The slit plate 152a having an aperture is provided for eliminating scattering light from other places than the inspection area 3 and for reducing noises.

The CCD control and signal reading circuit 155 is controlled by the data processing and control unit 13 via the interface 20 and the control unit 19, reads serially the detection signals detected in response to the intensity of receiving light and transmits the same to the A/D 17, wherein the detected signal is converted into a digital value which is then transmitted to the data processing and control unit 13 via the interface 20 as a detection signal (in digital value).

The detection optical system 15 is positioned in such a manner that an inspection area 3 is located at a position in Y direction corresponding to the head portion of the wafer 1 at the moment when the wafer 1 is started to move in the main scanning direction (Y direction). Since the wafer 1 is configured in a circular shape, a substantial part of the inspection area 3 can be placed outside the outer configuration of the wafer 1 at this head portion, the inspection area 3 is illustrated somewhat to the inner side in the X direction and somewhat to the inner side of the actual head portion of the wafer 1 for the sake of illustration and explanation convenience.

The data processing and control unit 13 is normally constituted by, for example, a MPU 131 and a memory 132, and receives the signals from the A/D 17 via the interface 20 and a bus 133 and stores the same in the memory 132. The memory 132 stores several types of programs including an extraneous substance detection program 134, a shading correction value setting program 135 and a focusing program (not shown). Further, the memory 132 includes a correction value table 136 in which correction values used for effecting shading correction for respective detection values are stored at corresponding positions to respective detecting pixels.

The table driving circuit 14 is a driving circuit which reciprocatively moves the inspection table 12 in the Y direction in response to the execution of the extraneous substance detection program 134 and shading correction value setting program 135 by the MPU 131. Further, at the moment when completing the movement corresponding to the wafer diameter D 1+α(α represents a margin for the scanning) in the Y direction, a Zθ table 122 is turned by 180° and the table driving circuit 14 causes the inspection table 12 to move backward corresponding to the diameter D+α in the Y direction. Namely, the table driving circuit 14 is a driving circuit which causes a reciprocative scanning over the wafer 1 in the Y direction and rotation (normal rotation and reverse rotation) thereof.

The inspection table 12 is constituted by a Y table 121, the Zθ table 122 and a center positioning mechanism 123 provided at the Zθ table 122. The center positioning mechanism 123 is a restriction mechanism including a plurality of rollers 124 arranged along the outer circumference of the wafer 1. Since the plurality of rollers 124 are designed to permit an interlocked rotation from the outside to the inside like shutter diaphrams, the center of the wafer 1 carried on the inspection table 12 is positioned at the center of the inspection table 12.

The Y table 121 is constituted by a base plate 125, rails 126 provided on the base plate 125, and a table 127 which is designed to be slidable on the rails 126 in the Y direction.

The Zθ table 122 is a table carried on the table 127 and movement of the Zθ table 122 in the Z direction is performed by an elevation mechanism provided inside the table 127 and secured thereto. The elevation mechanism primarily moves the wafer 1 in the vertical direction for focusing and sets the vertical position of the wafer 1. Before performing the extraneous substance detecting processing and the following shading correction value setting processing the MPU 13 executes the focusing program to effect focusing by the elevation mechanism.

Figure 2:
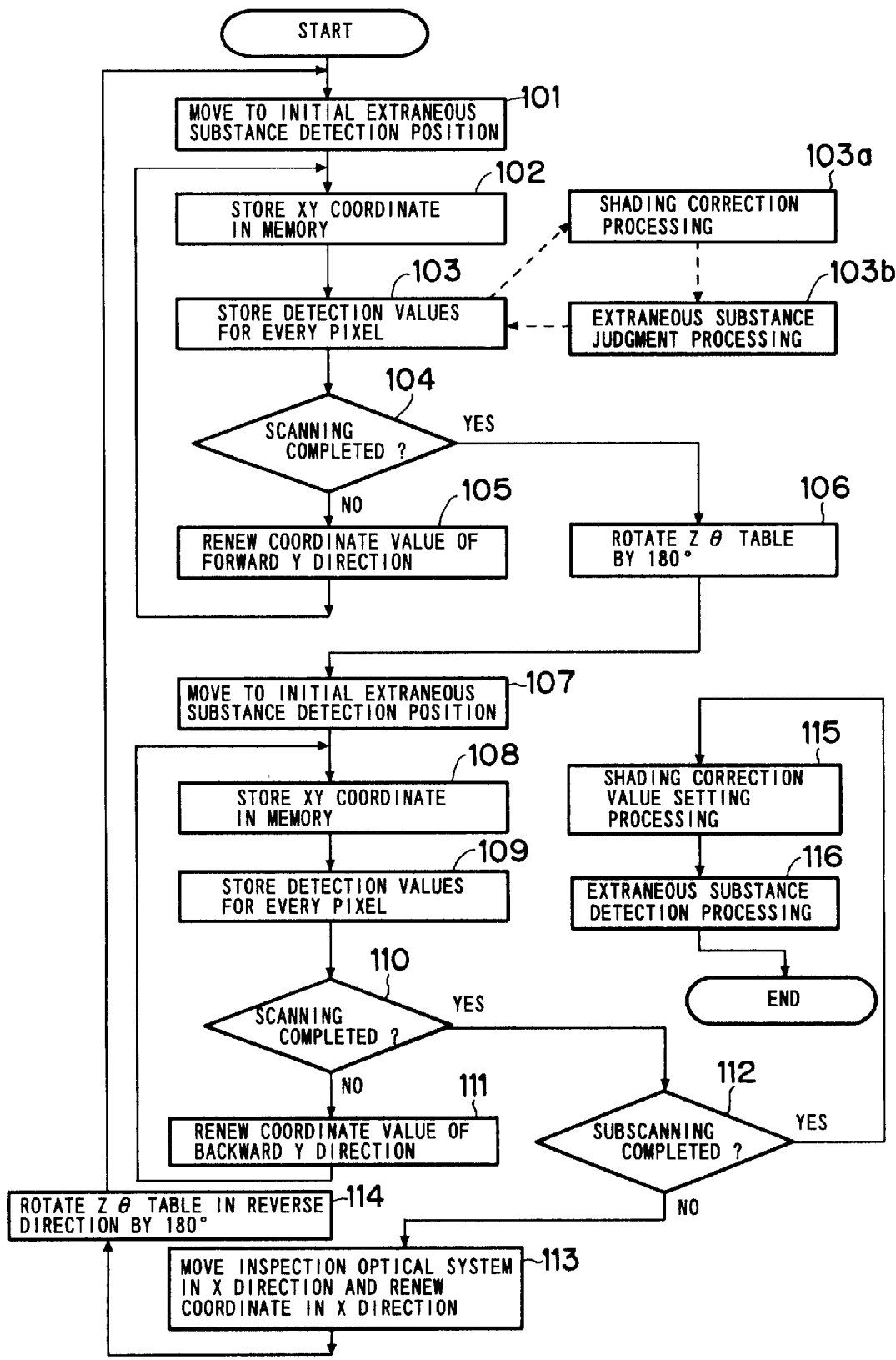
FIG. 2 is a flowchart for a shading correction value setting process.

FIG. 2 is a flowchart for correction value setting processing which is performed by the MPU 131 when executing the shading correction value setting program 135. During the shading correction value setting processing, like the processing with the extraneous substance detection program 134, the MPU 131 for the first time stores detection values (level of detection signals) in the memory 132 at positions corresponding to respective detection positions on the wafer 1 while performing XY scanning thereon. Secondly, the MPU 131 extracts respective detection positions (in XY coordinates) of each of light receiving element (detecting portions) during the XY scanning to determine average values thereof, then the average values of respective detection signals for optical elements representing the respective detecting pixels are used as shading values for the respective detecting pixels. Then, a reciprocal ratio of the shading value and a predetermined reference value is calculated to determine a correction value for each of the detecting pixels and the respective correction values are stored in the memory 132 for respective detecting pixels. Thereby, the MPU 131 sets correction values and performs shading correction for respective detection values of the respective detecting pixels based on the determined correction values during extraneous substance inspection.

On one hand, when the MPU 131 executes the extraneous substance detection program 134, to perform extraneous substance inspection, respective detection values which were subjected to shading correction by the respective correction values stored in the memory 132 are compared with a threshold value to thereby judge existence and non-existence of an extraneous substance at respective detection positions. Such judgment can be performed every time when a detection value is obtained. Alternatively, such judgment can be performed after completing XY scanning over the entire surface of a wafer which is an inspection object.

Now, detection positions are determined by detection positions (in XY coordinates) in the current XY scanning and by the positions of light receiving elements (detecting portions) in the CCD sensor 154 covering 5,000 pixels. Further, the detection values of respective light receiving elements disposed at respective detecting pixels are peak values of analog signals which are generated by the respective light receiving elements. For this reason, the intensity of the laser beam irradiated onto the inspection area 3 is regulated to a level which causes no saturation of light receiving values (detection values) of the light receiving elements at respective detecting pixel positions. The peak values can be determined, after A/D converting the outputs from the CCD sensor 154, based on the converted values as peak values for respective light receiving elements representing or corresponding to respective detecting pixels; alternatively, a peak detection circuit which detects peak values for the respective detecting pixels may be provided in the CCD control and signal reading circuit 155 to detect the peak values for the respective detecting pixels, and then the detected peak values are sent out to the A/D 17 where the peak values are converted into digital values.

Hereinbelow, a specific processing for the shading correction value setting is explained with reference to FIG. 2.

When the MPU 131 executes the shading correction value setting program 135 through inputting a predetermined function key for starting measurement, the Y table 121 is driven and a forward scanning in the Y direction is started. When the detection area 3 moves to the initial extraneous substance detection position (step 101), the MPU 131 stores the XY coordinate value of the current detection area 3 in the memory 132 (step 102), and subsequently, detection values (digital values showing peak levels of the detection signals at respective light receiving elements representing respective detecting pixels) of from the first pixel to the nth pixel determined in relation to light receiving positions (positions of light receiving elements) in the CCD sensor 154 are successively extracted and these values are successively, in that from the first pixel to the nth pixel, stored at corresponding positions of the respective detecting pixels in the memory 132 (step 103). Thereafter, the MPU 131 performs a judgment whether scanning in an amount of diameter D+α of the wafer 1 in the Y direction is completed (step 104). If such scanning is not completed, the judgment is NO and the MPU 131 causes Y table 121 to be moved further in the Y direction to renew the coordinate value in the Y direction (step 105), and the process again returns to the processing in step 102. Then, after routing steps 102 and 103 the MPU 131 again causes to perform the above judgment at step 104.

Through the recycling loop of steps 102~104 when one forward main scanning in the Y direction is completed, the judgment at step 104 changes to YES, then the MPU 131 causes the Zθ table 122 to rotate by 180° to reverse the same (step 106) and causes the Y table 121 to be driven in the reverse direction from the previous one to initiate a return scanning in the Y direction. Thereby, the detection area 3 moves to an initial extraneous substance detection position for the return scanning (step 107) and the MPU 131 stores the XY coordinate value for the current scanning in the memory 132 (step 108). Subsequently, as in step 103 the MPU 131 causes detection values (digital values showing peak levels of the detection signals) to be stored based on the detection signals received from the A/D 17 successively in relation to light receiving positions (positions of light receiving elements) in the CCD sensor 154 at corresponding positions to respective detecting pixels in the memory 132 (step 109). Thereafter, a judgment as to whether the return scanning in the Y direction in an amount of the diameter D+α of the wafer 1 is completed is performed (step 110). If not completed, the judgment is NO and MPU 131 causes the Y table 121 to be move further in the in return Y direction to renew the coordinate value in Y direction (step 111), the process again returns to the processing in step 108 and then after routing steps 108 and 109, the MPU 131 again causes the above scanning completion judgment to be performed at step 110.

Through the recycling loop from step 108 to step 110, when one returning main scanning in the Y direction is completed, the judgment at step 110 changes to YES. Thereby, the first time reciprocating scanning is completed.

Since the shading detection use wafer 1 is a circular shape, a part of the detection area lacks for the first reciprocating scanning in the Y direction, the detection signal values from pixels corresponding to the lacking part are excluded from the detection object. Further, these detection signal values are generally eliminated because the levels thereof are usually below a predetermined value. Still further, the first extraneous substance detection position for the scanning can be identified by detecting whether a detection signal level of any of the light receiving elements representing respective detecting pixels in the CCD sensor 154 exceeds a predetermined value.

Now, when the judgment in the previous step 110 turns to YES, the MPU 131 causes judgment processing as to whether the subscanning is completed (step 112). This judgment is performed to determined whether the extraneous substance inspection optical system 11 is positioned at a predetermined position in X direction. In this judgment, if a predetermined movement in the subscanning direction has not been completed, the MPU 131 causes the X direction movement mechanism 18 to move toward the inside of the wafer 1 by a predetermined subscanning amount corresponding to the inspection area 3 and to move the extraneous substance inspection optical system 11 by one pitch (an amount substantially corresponding to the width of the inspection area 3) in the subscanning direction to renew the X coordinate (step 113). Thereafter, the Zθ table 122 is rotated in the opposite direction by 180° to return the same to its original condition (step 114), and then the process returns to step 101 which is the first processing step, and the above explained processes are restarted and are repeatedly executed until the predetermined subscanning has been completed.

If it is judged at step 108 that the predetermined subscanning has been completed, the processing ends. The completion of the subscanning in step 112 is judged when the extraneous substance inspection optical system 11 moves toward the inside of the wafer 1 and either forward or backward scanning over the area including a center line passing the center of the wafer 1 has been performed, which represents the last scanning for the entire surface scanning of the wafer 1. In other words, the completion is judged when the extraneous substance inspection optical system 11 has been positioned at a predetermined position in the X direction. Further, through the 180° rotation of the Zθ table 122 at steps 106 and 114 the wafer is alternatively caused to rotate normally and reverse in the for every forward and backward main scanning.

Figure 5A:
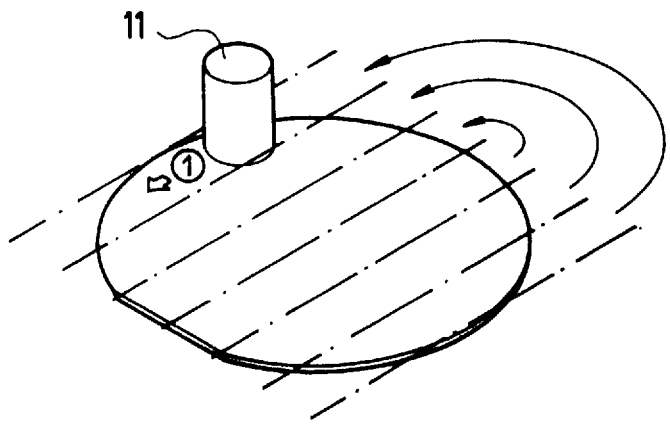
FIGS. 5(a), 5(b) and 5(c) are views for explaining rotation of a wafer and reciprocating scanning therefor.
Figure 5B:
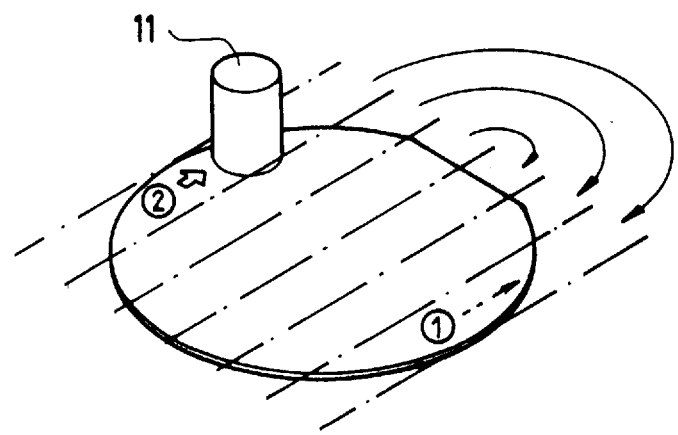
Figure 5C:
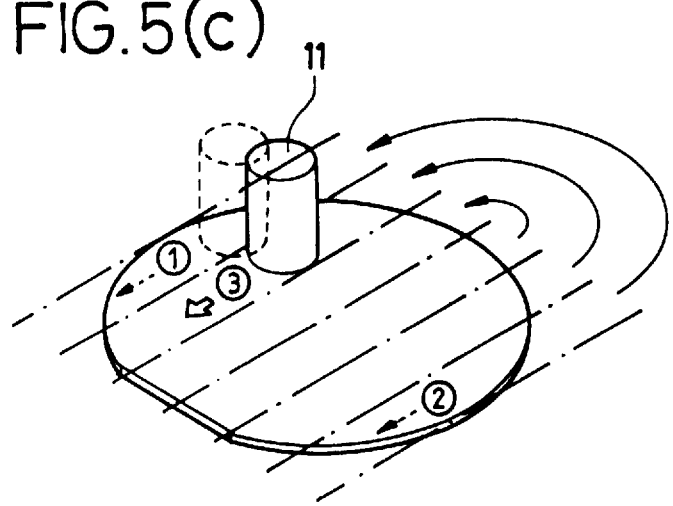

FIGS. 5(*a*) through 5(*c*) show the order of the forward and backward scanning in the above explained processing with numerals (1), (2) and (3). FIG. 5(*a*) shows the first forward scanning state, FIG. 5(*b*) shows the first backward scanning state and FIG. 5(*c*) shows the subsequent forward scanning state. As seen from FIG. 5(*c*), the scanning area on the wafer 1 results in the order of (1), (2) and (3). Arrows in FIGS. 5(*a*) through 5(*c*) represent directions of 180° rotation of the wafer 1 after completing respective main scannings.

In this embodiment, for the main scanning, the table moves reciprocally in the main scanning direction, whereby the table is alternatively rotated by 180° in normal and reverse directions at the time between the forward and backward scannings. However the table may be rotated by 180° in the same direction at the time between the forward and backward scannings. As a result, the scanning direction for the wafer 1 is equated for both the forward scanning and the backward scanning. In the drawings, dotted arrows indicate the directions of already completed scannings.

When it is judged in the previous step 112 that all of the scannings for the subscanning have been completed, the process moves to the shading correction value setting processing at step 115. At first, shading values (average values) of detection values for the respective detecting pixels are calculated and the shading correction value setting processing is performed based on the calculated result. The correction value setting in this instance is performed by successively storing correction values correcting the detection values for the respective detecting pixels from pixel No.1 to pixel No.5,000 successively in the order of the number in the correction value table 136 (see FIG. 4(*a*)). After setting these correction values the process moves to the extraneous substance detection processing (step 116).

Before explaining the details of the shading correction setting processing at step 115 which will be explained later, at first the extraneous substance detection processing is explained in which, as an inspection object to be mounted on the inspection table 12, an ordinary wafer is mounted in place of the shading detection use wafer to perform the wafer inspection. Then, during the respective forward and backward main scanning, the MPU 131 executes the extraneous substance detection program 134, multiplying the respective detection values (peak values) of the pixel No.1 to the pixel No.5,000 received successively from the A/D 17 in order, with respective correction values corresponding to the respective pixel Nos. stored in the correction value table 136 to effect the shading correction (step 103a). Then, it is judged based on the corrected values whether an extraneous substance exists in the inspection area 3 in relation to the light receiving position (light receiving element or detecting pixel position) in the CCD sensor 154, and, when an extraneous substance exists, how large the size thereof is (step 103b) to perform the extraneous substance detection.

The detail sequence of the extraneous substance detection processing is similar to the processing from step 101 to step 114. However, the detection values for all pixels at step 103 are subjected to the shading correction (step 103a), the judgment is performed whether the respective detection values subjected to the shading correction represent an extraneous substance (step 103b) and, based on the judgment result, the respective detection values subjected to the shading correction are stored in the memory 132 for every detecting pixel. Further, according to the judgment result when it is judged, for example, that a certain detection value subjected to the shading correction at step 103b represents an extraneous substance, a flag indicating existence of an extraneous substance is turned ON for the corresponding certain detection value.

Except for the above differences and non-inclusion of the shading correction value setting processing steps 115 and 116, the extraneous substance detection processings are substantially the same as the processing from step 101 to step 116. Therefore, the detailed explanation thereof is omitted.

Figure 3:
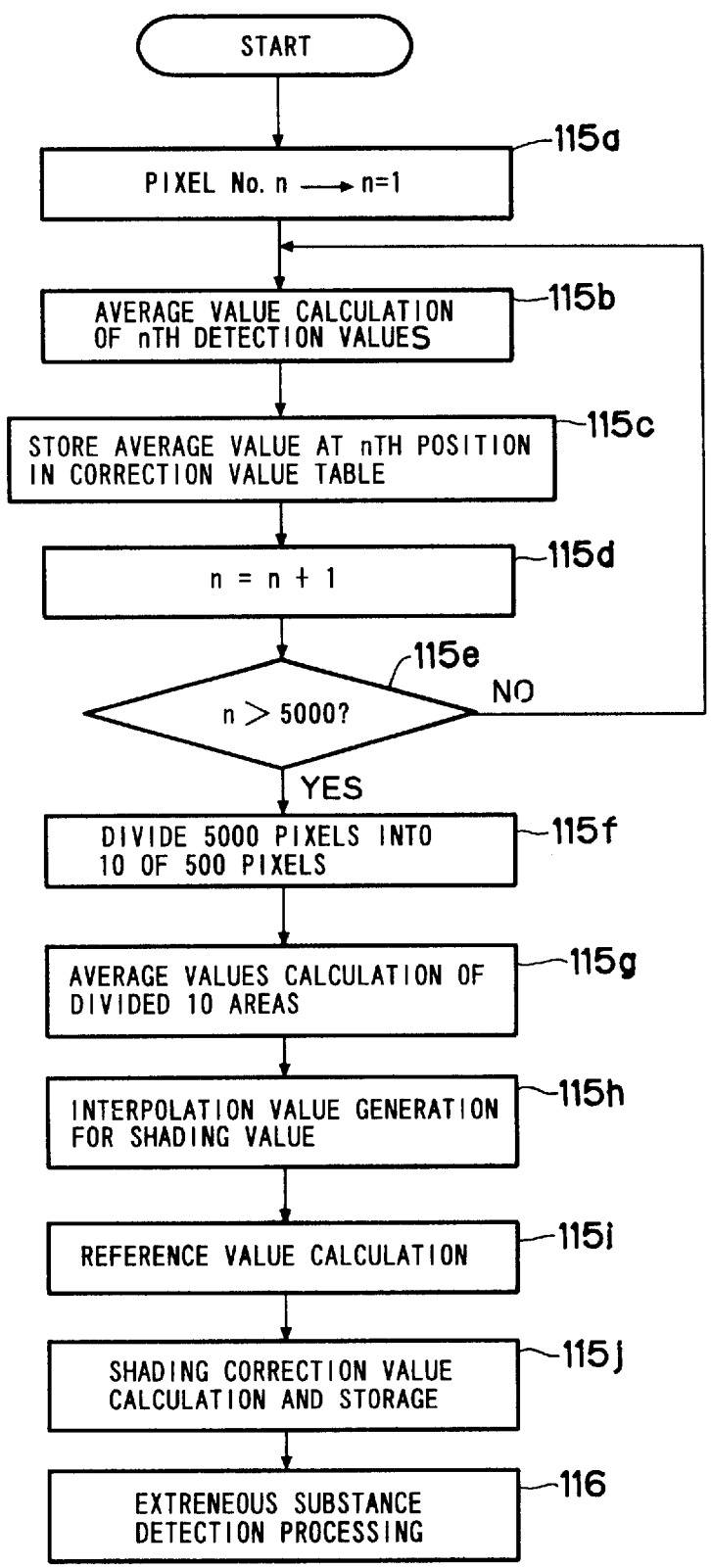
FIG. 3 is a flowchart for a shading correction value calculating process.

Hereinbelow, the details of the shading correction value setting processing at step 115 is explained with reference to FIG. 3.

At the moment when the scanning over the entire surface of the wafer 1 has been completed, the process by the MPU 131 moves to step 115 wherein at first average values for every detecting pixel are calculated from detection values for every pixel prior to the shading correction which were stored in the memory 132 at steps 103 and 109 in FIG. 2, and respective shading values are determined.

In this processing, at the first pixel No., parameter n for detection values is set at n=1 (step 115a). Secondly, the MPU 131 extracts the detection value of the nth pixel (at first, since n=1, the first one) from the detection value data for every detecting pixel stored in accordance with their corresponding XY coordinates in the memory 132, calculates its average value (step 115b), and stores the calculated average value at the position corresponding to pixel No. n in the correction value table 136 (step 1154c). Further, the MPU 131 renews the pixel No. to n=n+1 (step 115d), and judges whether or not the pixel No. n exceeds 5,000 (step 115e). In this judgment when the answer is NO, the process returns to step 115b and similar processings as above are repeated. When the result of judgment at step 115e changes to YES, the MPU 131 divides 5,000 pixels into 10 blocks, each having 500 pixels (step 115f), and determines average values (see fine lines in FIG. 4(b)) for respective divided 10 areas (step 115g). The bold line curve in FIG. 4(b) is one obtained by connecting respective shading values determined by averaging respective detection values for every detecting pixel in the CCD sensor 154. Again the vertical fine lines represent respective average values for respective divided areas (pixel No.1~pixel No.500, pixel No.501~pixel No.1,000, . . . pixel No.4,501~pixel No.5,000). These average values are respectively allotted to each pixel located at centers of respective divided areas. Namely, the respective average values are written at respective detecting pixel positions in the correction value table 136 corresponding to each center detecting pixel position in respective divided areas.

Of course, the shading correction values can be calculated by making use of the shading values indicated by a bold line in FIG. 4(b). However, in the present embodiment a shading value used as a correction value is determined by making use of further interpolation values. This is because the bold line shading values are determined only by scanning one entire surface, so that even if the shading values are determined by averaging respective detection values for every detecting pixel, influences of detection circumstances for the respective individual detecting pixels still remain. Therefore, in order to set normal average correction values the area is divided into a plurality of blocks and average values for the respective blocks are determined. Thereby, interpolation values which approximate the bold line are generated with reference to these average values and more general shading values are obtained. Such division of the CCD representing pixels into blocks is effective if more than 1,000 pixels are included in the CCD sensor 154.

Accordingly, an interpolation value is generated based on three average values of successive divided areas and the data on respective pixels between the three averages in the correction value table 136 are modified. Thereby, the shading value generation processing by making use of interpolation values is performed (step 115h). In this step, the interpolation values are generated by making use of the average values of respective areas as the values at the center pixels of the respective areas, namely at the 250th pixel, 750th pixel, 1250th pixel, . . . 4750th pixel. The interpolation values are represented by a polygonal line graph illustrated in FIG. 4(c) which is formed by connecting the respective tops of the fine vertical lines in FIG. 4(b) by respective straight lines. However, since no average value exists prior to that of the first pixel, the detection value for the first pixel is assumed as the average value for the area prior to the first pixel; similarly, since no subsequent area for the last 5,000th pixel exists, the detection value for the 5,000th pixel is assumed as the average value for the subsequent area. Further for the pixels other than the above, from 251st pixel to the 4749th pixel respective interpolation values are generated by incrementally adding a value, determined by dividing the difference between average values of the respective successive areas by 499 (500-1), to the value of the center pixel in the prior area every time when pixel number increases one. Thereby, in place of the shading values indicated by the bold line for respective detecting pixels assigned to respective actual detecting portions in the CCD sensor 154, the shading values represented by the polygonal line illustrated in FIG. 4(c) which are formed by connecting the respective tops of the vertical fine lines are obtained.

Subsequently, correction values which are set for every detecting pixel assigned to a respective detecting portion in the CCD sensor 154 are calculated. Namely, at first one reference value is determined by selecting one among an average value, maximum value and minimum value of the detection values of 5,000 pixel components represented as shading values and illustrated in the bold line in FIG. 4(a), among a further average value, a further maximum value and a further minimum value of the average values calculated for the respective divided areas and among a predetermined value, then respective reciprocal ratios are calculated by using the above selected reference value as a numerator and the shading values for respective detecting pixels determined at step 115h as a denominator, and the calculated values are successively stored at respective corresponding detecting pixel Nos. in the correction value table 136 (step 115j) and which correspond to the shading correction values for the respective detecting pixels in the correction value table 136 illustrated in FIG. 4(a). Further, although a variety of values can be employed for the above reference value which is used for calculating the shading correction value, in the present embodiment an average M as illustrated by a broken line in FIG. 4(c) is employed as the reference value.

In the above explained embodiment, interpolation values for every pixel in a certain divided area are calculated by making use of average values of respective divided pixel areas and then shading correction values for every detecting pixel are calculated based on the calculated interpolation values for every detecting pixel as representing the shading values.

In a general use surface defect inspection device such as for liquid crystal substrates and magnetic disks, the surface defects which are the inspection objects include pits (recessed defects), mounds (projecting defects) and extraneous substances caused by depositing external particles, wherein the pits include dimples, craters, slit shaped scratches, channel holes, teared flaws and small dots, and the mounds include bumps. Further, other than the above defects, stains and dirts on the surface thereof are also treated as one of defects. In this connection, in case of an extraneous substance inspection device such as for wafers, scratches, channel holes, and tear flaws rarely occur and extraneous substances which likely cause defects are dominating; however, an extraneous substance inspection device deals with the above indicated general defects as extraneous substances and takes the same as detection objects.

As explained with reference to the present embodiment, the present invention is directed to shading correction for optical sensors in a defect inspection optical system. The shading correction is commonly required for a defect inspection performed by receiving reflection light through optical sensors including CCD sensors in which a multiplicity of detecting pixels are arranged in a straight line. Accordingly, the present invention is not limited to the wafer extraneous inspection device as illustrated in connection with the present embodiment, but also can be applied to a variety of general surface defect inspection devices.

We claim:

1. A surface defect inspection device, comprising:
   a main and subscanning mechanism;
   a defect inspection optical system including a defect inspection area of a predetermined width in a subscanning direction for an object to be inspected, and an optical sensor which receives reflected light from the defect inspection area with every detecting pixel and generates detection signals of every detecting pixel;
   a defect detection unit which causes said main and subscanning mechanism to scan the object to be scanned with said defect inspection optical system;
   an article corresponding to the object to be inspected, said article having a multiplicity of substantially uniformly distributed standard particles deposited thereon, wherein said defect inspection unit includes an average value calculating means in which the article is scanned in a main scanning direction as a defect inspection object, detection values of the standard particles at every detecting pixel are obtained based on detection signals obtained from the optical sensor at respective scanning positions while assuming the standard particles as being defects, and average values of every detecting pixel with regard to the detection values obtained at the respective scanning positions are calculated; and
   a shading correction means in which detection values of every detecting pixel obtained when the object to be inspected is inspected are subjected to shading correction for every detecting pixel based on the calculated average values of every detecting pixel calculated for the article corresponding to the object to be inspected.

2. A surface defect inspection device according to claim 1, wherein said object to be inspected is a semiconductor wafer, said defect inspection optical system is an extraneous substance detection optical system, said article is a blank semiconductor wafer on a surface of which the standard particles are deposited, and said optical sensor includes a plurality of light receiving elements arranged in a straight line in subscanning direction, each of said light receiving elements corresponding to one of said every detecting pixel.

3. A surface defect inspection device according to claim 2, further comprising a memory which stores the average values of every detecting pixel at positions for every detecting pixel.

4. A surface defect inspection device according to claim 3, further comprising a shadow correction value calculating means for performing the shading correction, wherein said shading correction value calculating means selects a reference value from one of a predetermined constant value, an average of the detection values for every detecting pixel, a maximum value of the detection values for every detecting pixel, and a minimum value of the detection values for every detecting pixel; calculates reciprocal ratios of the selected reference value and the average values for every detecting pixel, as correction values for every detecting pixel and stores the calculated correction values in said memory in place of the average values for every detecting pixel; and said shading correction means corrects for every detecting pixel the detection values of every detecting pixel obtained when the object to be inspected n inspected based on the correction values stored in said memory.

5. A surface defect inspection device according to claim 4, wherein the number of the detecting pixels is more than 1,000, and said average value calculating means divides the entire detecting pixels into a plurality of block, calculates average values of the detection values for every blocks, and calculates interpolation values for respective detecting pixels in a certain block based on the average value of the certain block and average values of adjacent blocks with the certain block to determine average values for every detecting pixel.

6. A surface defect inspection device according to claim 5, further comprising a processor, wherein said average value calculating means, said shading correction means and said shading correction value calculating means are realized through execution of programs stored in said memory by said processor.

7. A surface defect inspection device according to claim 6, wherein said optical sensor is a CCD sensor and said correction values are stored in a table for every detecting pixel.

8. A shading correction method of an optical sensor for a surface defect inspection device in which a defect inspection area having a predetermined width in a subscanning direction for an object to be inspected is set, reflection light from the defect inspection area is received by the optical sensor through every detecting pixel therein arranged in the subscanning direction, detection signals of every detecting pixel are generated from the optical sensor, and a defect of the object to be inspected is detected by scanning the object to be inspected and receiving the detection signals, comprising the steps of:

scanning in a main scanning direction an article corresponding to the object to be inspected, said article having a multiplicity of substantially uniformly distributed standard particles deposited thereon;

obtaining detection values of the standard particles at every detecting pixel based on the detection signals obtained from the optical sensor at respective scanning positions while assuming the standard particles as being defects;

calculating average values of every detecting pixel with regard to the detection values obtained at the respective scanning positions; and subjecting detection values of every detecting pixel obtained when the object to be inspected is inspected to shading correction for every detecting pixel based on the calculated average values of every detecting pixel calculated for the article corresponding to the object to be inspected.

9. A shading correction method for a surface defect inspection device according to claim 8, wherein the article is a blank semiconductor wafer on a surface of which the standard particles are deposited, and the optical sensor includes a plurality of light receiving elements arranged in a straight line in the subscanning direction, each of said light receiving elements corresponding to one of said every detecting pixel.

10. A shading correction method for a surface defect inspection device according to claim 8, further comprising:

selecting a reference value from one of a predetermined constant value, an average of the detection values for every detecting pixel, the maximum value of the detection values for every detecting pixel, and the minimum value of the detection values for every detecting pixel; and calculating reciprocal ratios of the selected reference value and the average values for the every detecting pixel as correction values for every detecting pixel to perform the shading correction.

* * * * *